United States Patent [19]

Ostensen et al.

[11] Patent Number: 4,725,268
[45] Date of Patent: Feb. 16, 1988

[54] VENTED ANTI-REFLUX VALVE

[75] Inventors: Ralph Ostensen, Northbrook, Ill.; Mark McGlothlin, San Diego, Calif.

[73] Assignee: Baxter Travenol Laboratories, Inc., Deerfield, Ill.

[21] Appl. No.: 878,169

[22] Filed: Jun. 25, 1986

[51] Int. Cl.⁴ .............................................. A61M 1/00
[52] U.S. Cl. .................................... 604/323; 604/129; 604/247; 604/326; 137/588; 383/45
[58] Field of Search ............... 604/323, 324, 335, 350, 604/247, 325, 126, 333, 327–329, 355, 326, 128, 129; 383/45; 128/760, 767, 769; 137/588; 55/159

[56] References Cited

U.S. PATENT DOCUMENTS

| | | | |
|---|---|---|---|
| 3,529,599 | 9/1970 | Folkman et al. | 604/323 |
| 3,800,795 | 4/1974 | Walker | 604/323 |
| 3,998,255 | 12/1976 | Mather et al. | 604/324 |
| 4,160,383 | 7/1979 | Rauschenberger | 604/323 |
| 4,193,399 | 3/1980 | Robinson | 55/159 |
| 4,412,916 | 11/1983 | Kell | 55/421 |
| 4,490,144 | 12/1984 | Steigerwald | 604/323 |
| 4,512,770 | 4/1985 | Cianci et al. | 604/323 |
| 4,533,354 | 8/1985 | Jensen | 604/323 |
| 4,636,313 | 1/1987 | Vaillancourt | 604/126 |

FOREIGN PATENT DOCUMENTS

| | | | |
|---|---|---|---|
| 0246701 | 9/1963 | Australia | 383/45 |
| 2078113 | 1/1982 | United Kingdom | 604/326 |
| 2111391 | 7/1983 | United Kingdom | 604/129 |

Primary Examiner—Dalton L. Truluck
Assistant Examiner—Mario Costantino
Attorney, Agent, or Firm—Roger A. Williams; Paul C. Flattery; Robert E. Hartenberger

[57] ABSTRACT

A combination anti-reflux valve and gas venting device for use in a urinary drainage bag is described. In the preferred embodiment, the device is made of a flapper valve having a gas venting portion inside the urinary drainage bag. The flapper valve is connected to a gas venting connector means for passage of gas between the outside and inside connector means.

23 Claims, 5 Drawing Figures

FIG. 2
FIG. 3
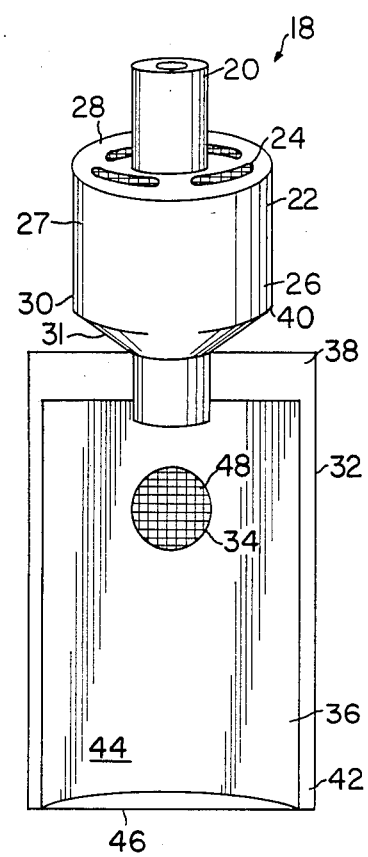
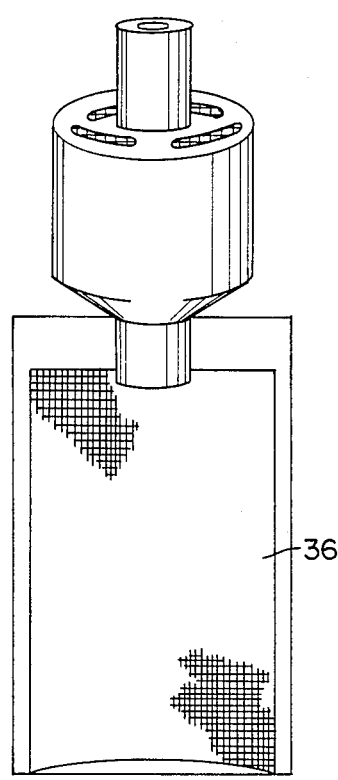
FIG. 4
FIG. 5
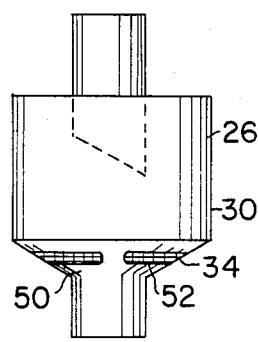
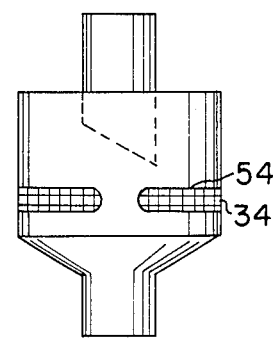

VENTED ANTI-REFLUX VALVE

BACKGROUND OF THE INVENTION

The invention generally relates to combination gas venting and anti-reflux devices and more specifically relates to such devices when used in urinary drainage bags.

Urinary drainage bags are commonly made from two flat sheets of flexible plastic sealed together at their edges. Typically, urinary drainage bags have a potential capacity of approximately 2,000 ml. Depending on the shape of the two flat sheets, it may be necessary to allow air into the bag as the bag begins to fill with liquid, to assist in the separation of the two sheets comprising the bag. During use of the bag, an undesirably high positive pressure can develop in the bag after the bag has expanded to its maximum potential volume. If this positive pressure exceeds the static pressure of a patient's bladder (which is approximately 10 cc. water head height), the flow of urine out of the bladder and into the bag can be impeded or stopped. Therefore, it is commonly desired to provide a means of venting gas from the inside of the urinary drainage bag to the atmosphere to prevent such undesirably high pressure from occurring in the bag.

Another feature common to urinary drainage systems is to provide an anti-reflux or one-way valve either at an inlet to the urinary drainage bag or in a drainage tube between a patient and the bag. The function of this valve is to prohibit urine in the bag from flowing back into the bladder if the bag is inadvertently raised above the level of the patient's bladder. This is particularly important if infectious organisms are present, or if high dosages of antimicrobial materials that are potentially harmful to the bladder are in the bag.

A logical location for an anti-reflux valve is at the bag inlet port. Unfortunately if the anti-reflux valve is very effective, it is also an effective barrier so as to prevent gas from venting between the inside of the bag and any gas venting means that may be present in the drainage tube. Therefore, at least three critical and costly components are typically present in a urinary drainage bag. One component being an anti-reflux valve, a second component being a separate gas venting means for venting gas between the inside of the bag and the atmosphere, and a third component being a gas venting means between the drainage tube and the atmosphere. Thus, if a urinary drainage bag includes an anti-reflux valve, a single gas vent is typically not considered to be sufficient; two separate gas vents have been commonly used. One gas vent is used to vent gas in the drainage tube upstream of the anti-reflux valve, and a separate gas vent (typically located on a wall of the drainage bag) is used to vent gas in the bag downstream of the anti-reflux valve.

U.S. Pat. No. 4,334,537 to Peterson is representative of a typical three-component urinary drainage system having two separate vents as well as an anti-reflux valve. As can be seen in FIG. 1 of the Peterson patent, a connector 30 may be provided which contains vent 32 which can vent gas in a drainage tube to the atmosphere. The connector may also contain an anti-reflux mechanism as illustrated in FIG. 2. It should be noted that a separate vent 20 is required in this type of system to vent any gas present in the drainage bag to the atmosphere.

U.S. Pat. No. 4,512,770 to Cianci et al., and U.S. Pat. No. 3,604,420 to Vaillancourt also describes similar arrangements.

OBJECTS OF THE INVENTION

In view of the foregoing, it is an object of the invention to provide a combination anti-reflux valve and gas venting means in a single component to provide for one-way passage of fluid into a urinary drainage bag, and to provide for passage of gas between the atmosphere and the inside of the urinary drainage bag.

It is another object of the invention to provide a combination anti-reflux valve and gas venting means which is relatively inexpensive and easy to manufacture.

It is yet another object of the invention to provide a gas venting means which is capable of venting gas between the urinary drainage bag and the atmosphere when the difference in pressure between the inside of the urinary drainage bag and the atmosphere is greater than 10 cc. water.

SUMMARY OF THE INVENTION

A device is described for venting gas between the inside and outside of a container. The device also provides for one-way flow of fluids into the container. The device includes an inlet port for passage of fluid into the container. A connector means is also provided in the device downstream of the inlet port for receiving fluid from the inlet port. The connector means has a first gas-venting means for venting gas between the connector means and the outside. An anti-reflux means is also provided in the device downstream of the connector means for allowing one-way passage of fluid to flow from the connector means into the container. In one embodiment of the invention, the anti-reflux means has a second gas-venting means for venting gas between the container and the connector means. In another embodiment of the invention, the connector means includes a second gas-venting means for venting gas between the container and the connector means. In the preferred embodiment of the invention, this device is used in combination with a urinary drainage bag to provide for one-way flow of urine from a drainage tube connected to a patient into the drainage bag while providing for venting of gas between the inside of the drainage bag and the atmosphere.

BRIEF DESCRIPTION OF THE DRAWINGS

FIG. 2 illustrates one embodiment of the subject invention in which a gas vent in the form of a disc is located in a flapper valve;

FIG. 3 illustrates another embodiment of the invention in which an entire "flapper" valve is made from a gas venting material;

FIG. 4 illustrates one embodiment of the invention in which a gas vent is located on an underside of a connector; and FIG. 5 illustrates another embodiment of the invention in which gas vents are located on a side wall of a connector.

DETAILED DESCRIPTION OF THE PREFERRED EMBODIMENT

Figure 1:
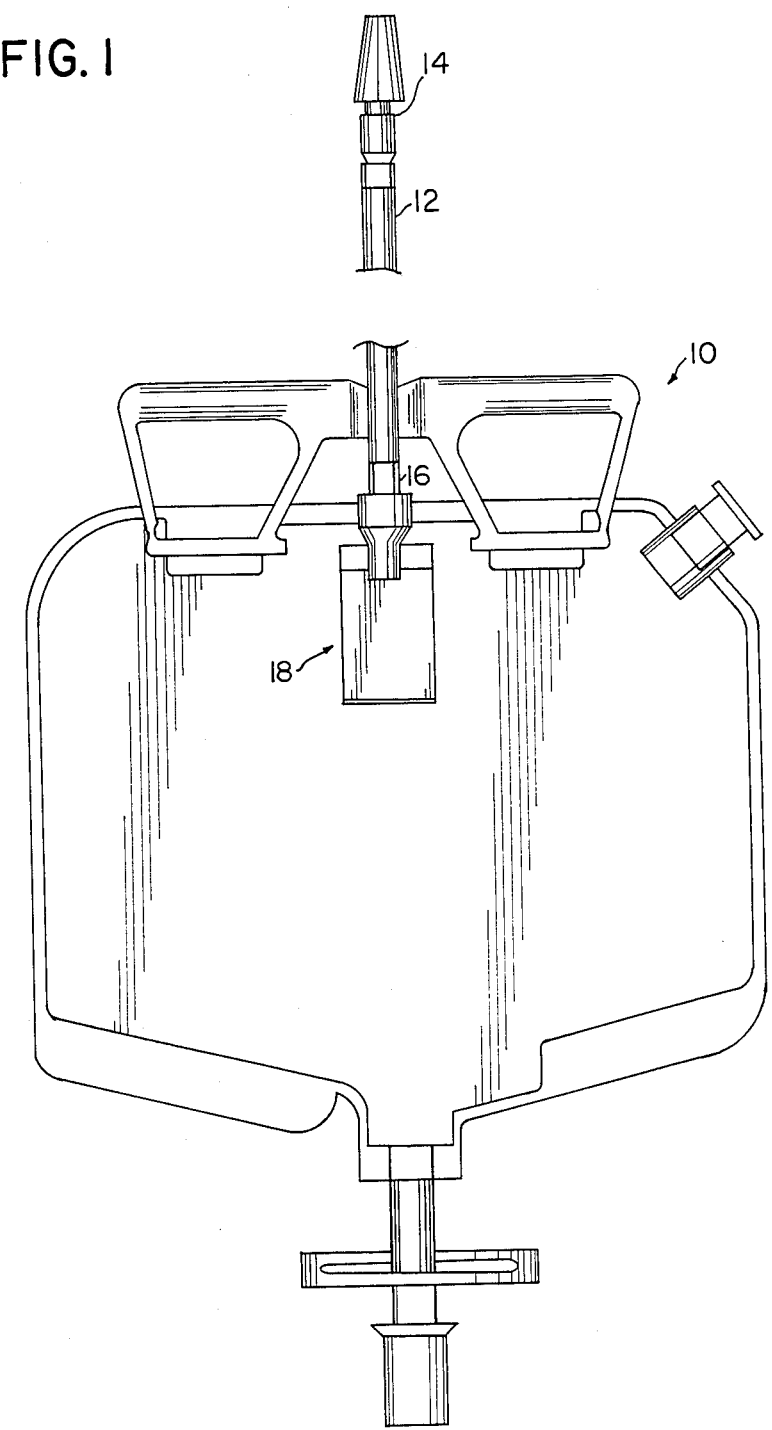
FIG. 1 illustrates the use of the subject invention in a urinary drainage bag.

Refer now to FIG. 1 which illustrates a urinary drainage bag 10 which includes a drainage tube 12. One end 14 of the drainage tube 12 may be connected to a urinary catheter (not shown) which receives urine from a patient. The other end 16 of the drainage tube may be connected to a device 18 for venting gas both between the inside and outside of a bag 10 and between the inside and outside of the drainage tube 12, as well as for providing for one-way flow of fluids into the bag. Various embodiments of the device 18 are illustrated in FIGS. 2 through 5.

Refer now to FIG. 2 which is the currently preferred embodiment of the invention. As can be seen in FIG. 2, the device includes an inlet port 20 for receiving fluid from the drainage tube 12. The inlet port is in fluid communication with a connector means 22 for receiving fluid from the inlet port. The connector means 22 includes a first gas venting means 24 for venting gas between the connector means 22 and the atmosphere.

As can be seen in the figure, in the preferred embodiment, the connector means 22 is a generally hollow cylindrical housing 26 which may be formed of plastic. The housing 26 may include a hollow cylindrical side portion 27 and a disc-shaped top portion connected to a first end of the cylindrical side portion. The top wall is in fluid communication with the inlet port 20. The connector 22 is disposed in the urinary drainage bag 10 in such a manner that a first portion of the connector 28 is located outside of the bag 10 and a second portion 30 is located inside the bag 10. The first gas venting means 24 is located in the first portion 28 of the connector 22 so that gas can be vented from the inside of the cylindrical housing 26 to the outside. In the preferred embodiment, the gas venting means 24 is located in the disc-shaped top portion. The gas venting means 24 may include a plurality of gas vents formed from a hydrophobic material which will pass gas, but will inhibit the flow of fluids therethrough. As can be seen from FIGS. 2 and 3, these vents may be in the shape of elongated chambers disposed about the first portion 28 of the connector means 22. In another embodiment, vent 24 may be in the form of a single doughnut-shaped section disposed about the inlet port. The connector means 22 also includes a bottom wall 31 connected to a second end of the cylindrical side portion 27.

In accordance with the invention, the device 18 also includes an anti-reflux means 32 downstream of, and in fluid communication with, the second portion of the connector means 22 to allow one-way passage of fluid from the connector means 22 into the bag 10. The anti-reflux means 32 includes a second gas venting means 34 for venting gas between the urinary drainage bag 10 and through the anti-reflux means to first gas venting means 24 on the connector means 22. Both the first gas venting means and the second gas venting means will allow the passage of gas, but will inhibit the passage of fluids through the venting means.

In the preferred embodiment, the anti-reflux means is formed from a flapper valve 36 having a first end 38 attached in open fluid communication with the second portion 30 of the connector means. The flapper valve includes a second end 42 having opposing walls 44 and 46 normally biased to be in contact with each other to prevent fluid flow from the bag 10 through the anti-reflux means to the connector 22. However, since the first end 38 of the flapper valve is in open fluid communication with the connector means, fluid will readily flow from the connector means 22 into the anti-reflux means. When pressure from fluid in the anti-reflux means exceeds the normal bias pressure on the opposing walls, the opposing walls will separate to allow fluid to flow from inside the anti-reflux means into the bag.

In one embodiment of the invention as illustrated in FIG. 2, one wall of the flapper valve includes an orifice 48. The orifice 48 is covered with a hydrophobic material which inhibits the flow of liquids therethrough, but will allow the passage of gas to act as the second gas venting means 34. In the preferred embodiment, the gas venting material is a hydrophobic microporous polypropylene layer of material. This layer is supported by a layer of microporous polyethylene which is in the form of a fibrous mat. If the walls of the flapper valve are made of polyvinyl chloride, the polyethylene mat, together with the polypropylene layer, can be heat sealed to one wall of the flapper valve along the periphery of the orifice 48. While the size of the vent 34 may vary, in the preferred embodiment the vent has a surface area of at least 3% of the surface area of the flapper valve. The size of the vent is related to the rate at which gas may pass between the inside of the bag 10 and the connector 22.

As can be seen in FIG. 3, in another embodiment of the invention, it may be desirable to have the entire flapper valve 36 made up of a gas-permeable material so that the flapper valve acts both as an anti-reflux means and as a gas venting means. The gas-permeable material may consist of a hydrophobic microporous polypropylene layer of material supported by a polyethylene mat.

In yet another embodiment of the invention as illustrated in FIG. 4, the second gas venting means 34 may be located in the second portion 30 of the connector housing 26. In this embodiment, the connector means includes a second end 50 which contains at least one orifice 52 for providing gas communication between the inside of the cylindrical housing 26 of the connector and the inside of the urinary drainage bag 10. The orifice is covered with a gas-permeable material that will pass gas and will inhibit the flow of fluids therethrough. This gas-permeable material may be similar to the material described above with respect to FIG. 2, or may be in the form of a thicker gas-permeable plug.

In yet another embodiment of the invention, the second venting means 34 may be located in the hollow cylindrical side wall portion 27 of the housing 26. This is illustrated in FIG. 5. In this embodiment, the side wall portion 27 includes at least one orifice 54 for communication between the inside of the housing 26 of the connector and the interior of the urinary drainage bag 10. This orifice is covered with a gas-permeable material similar to the material described with respect to FIG. 2 or FIG. 4.

As can be seen from the foregoing, the invention provides for a combination venting and anti-reflux device specifically designed for use with a urinary drainage bag. This device eliminates the need of a separate vent located on a wall of the urinary drainage bag to pass gas from the inside of the urinary drainage bag to the atmosphere.

This application describes three methods for combining the function of venting the drainage tube above an anti-reflux valve and venting the inside of a urinary drainage bag in one assembly. This substantially reduces the cost of manufacturing the device, and at the same time maintains optimal urine flow and safety for the patient.

Although the invention has been described and illustrated in detail, it is to be clearly understood that the same is by way of illustration and example only, and is not to be taken by way of limitation; the spirit and scope of the invention being limited only the terms of the appended claims.

We claim:

1. A device for venting gas between the interior of a container and the atmosphere and for providing one-way flow of fluids into the container comprising:
   a container having an interior for receiving a liquid;
   an inlet port;
   connector means for providing a fluid pathway connecting said interior of said container with said inlet port, said connector means located between the container and the inlet port said connector means having an interior and an exterior, and having a first portion disposed outside of said container, said first portion having a first gas venting means for venting gas between the interior of said connector means and the atmosphere, said connector means also having a second portion located in said interior of said container, said first and second portions being in fluid communication with one another; and
   anti-reflux means disposed in said interior of the container for allowing one-way passage of liquid to flow from the connector means into the container, said anti-reflux means including a flapper valve having a first end attached in open fluid communication to said second portion of said connector means and a second end in fluid communication with said interior of said container, said second end of said anti-reflux means having opposing walls normally biased to be in contact with each other to prevent liquid flow from said interior of said container to said interior of said connector means, but to allow fluid flow from said interior of said connector means to said interior of said container, said anti-reflux means having a second gas venting means provided on a portion of at least one wall of said flapper valve for venting gas between said interior of said container and said interior of said connector means to vent to the atmosphere through said first gas venting means and wherein the second gas venting means further includes a first portion made of a gas-permeable, hydrophobic material.

2. A device as recited in claim 1 wherein said hydrophobic material is microporous polypropylene.

3. A device as recited in claim 1 wherein said second gas venting means further includes:
   a first layer of hydrophobic microporous material; and
   a second layer of material for supporting said first layer.

4. A device as recited in claim 3 wherein said first layer consists of microporous polypropylene and said second layer consists of polyethylene.

5. A device as recited in claim 1 wherein:
   said walls of said flapper valve are made of polyvinylchloride; and
   said second venting means includes a first layer of microporous polypropylene and a second layer of polyethylene for supporting said first layer and for bonding to said polyvinylchloride.

6. A device as recited in claim 5 wherein one wall of said flapper valve has an orifice having an area of at least 3% of the surface area of said flapper valve and said second venting means further includes said first and second layers covering said area of said orifice.

7. A device as recited in claim 5 wherein one wall of said flapper valve has an orifice having an area between 3 and 99% of the surface area of said flapper valve said second venting covers said area of said orifice means.

8. A device as recited in claim 5 wherein said second venting means is heat sealed to at least one of said walls of said flapper valve.

9. A device as recited in claim 1 wherein:
   said flapper valve includes an orifice on at least one wall, said second venting means attached to the flapper valve so as to cover said orifice.

10. A device as recited in claim 9 wherein:
    said second venting means includes a first layer of microporous polypropylene and a second layer of polyethylene for supporting said first layer; and
    said flapper valve is made of polyvinylchloride, said second layer being heat sealed over an orifice in said polyvinylchloride.

11. A device as recited in claim 1 wherein said opposing walls of said flapper valve are made entirely of a gas permeable material to form said second gas venting means.

12. A device as recited in claim 11 wherein said gas-permeable material further includes:
    a first layer of microporous material; and
    a second layer of material for supporting said first layer.

13. A device as recited in claim 12 wherein said first layer consists of microporous polypropylene and said second layer consists of polyethylene.

14. A device as recited in claim 1 wherein at least one wall of said flapper valve is made entirely of a gas-permeable material to form said second gas venting means.

15. In a urinary drainage bag for receiving urine from a drainage tube, an improvement comprising:
    a fluid inlet port in fluid communication with said drainage tube;
    connector means having an interior and an exterior, said connector means located between the bag and the inlet port for receiving fluid from said inlet port, said connector means having a first portion located outside of said bag, said first portion having a first gas venting means for venting gas between said interior of said connector means and the outside; and
    anti-reflux means disposed in said interior of said bag and including a flapper valve having a first end attached in open fluid communication to the connector means and a second end in fluid communication with said interior of said bag, said second end having opposing walls normally biased to be in contact with each other to prevent liquid flow from said bag to said connector means, but to allow liquid flow from said connector means to said bag, said anti-reflux means having a second gas venting means on a portion of at least one wall of said flapper valve for venting gas between said bag and said connector means said second gas venting means further including a first portion made of gas permeable, hydrophobic material.

16. A device as recited in claim 15 wherein said hydrophobic material is microporous polypropylene.

17. A device as recited in claim 15 wherein said first portion of said second gas venting means further includes:
    a first layer of microporous material; and a second layer of material for supporting said first layer.

18. A device as recited in claim 15 wherein said first layer consists of microporous polypropylene and said second layer consists of polyethylene.

19. A device as recited in claim 18 wherein:
said walls of said flapper valve are made of polyvinylchloride; and
said second venting means includes a first layer of microporous polypropylene and a second layer of polyethylene for supporting said first layer and for bonding to said polyvinylchloride.

20. A device as recited in claim 19 wherein:
said second venting means further includes said first and second layers in the form of a disc having a surface area of at least 3% of the surface area of said flapper valve.

21. A device as recited in claim 19 wherein:
said second venting means has a surface area between 3 and 99% of the surface area of said flapper valve.

22. A device as recited in claim 19 wherein:
said second venting means is heat sealed to at least one of said walls of said flapper valve.

23. A device as recited in claim 15 wherein said flapper valve includes:
an orifice on at least one wall; and
said second venting means attached to the flapper valve so as to cover said orifice.

* * * * *